United States Patent
Wei et al.

(10) Patent No.: US 6,284,472 B1
(45) Date of Patent: Sep. 4, 2001

(54) METHOD FOR EXTENDING THE RANGE OF AN IMMUNOASSAY

(75) Inventors: Tie Quan Wei, Bear; Thomas John Pankratz, Newark; Victor Pichai Chu, Hockessin, all of DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/294,489

(22) Filed: Apr. 20, 1999

Related U.S. Application Data (63) Continuation-in-part of application No. 09/166,026, filed on Oct. 5, 1998, now abandoned.

(51) Int. Cl.⁷ .................. G01N 33/53; G01N 33/543; G01N 21/00; A61K 49/00; C07K 16/00
(52) U.S. Cl. .................. 435/7.1; 435/7.94; 435/7.93; 435/7.95; 435/962; 435/973; 435/795; 436/164; 436/34; 436/43; 436/50; 436/517; 436/518; 436/523; 436/524; 436/538; 436/546; 436/800; 436/805; 436/808; 436/817; 436/901; 422/50; 422/62; 422/67; 422/68; 422/61; 422/82.08; 424/7.1; 530/389
(58) Field of Search .................. 422/119, 50, 62, 422/67, 68.1, 61, 82.08; 436/34, 43, 50, 164, 817, 901, 517, 546, 518, 800, 523, 538, 824, 805, 808; 435/7.1, 7.93, 7.94, 7.95, 962, 973, 975; 424/7.1; 530/389, 390, 807

(56) References Cited

U.S. PATENT DOCUMENTS

| | | |
|---|---|---|
| 4,055,752 | 10/1977 | Kappe et al. ........................ 364/551 |
| 4,169,125 | 9/1979 | Rodriguez et al. .................... 422/65 |
| 4,358,852 | 11/1982 | Wu ...................................... 435/7.94 |
| 4,595,661 | 6/1986 | Cragle et al. ......................... 436/534 |
| 4,743,542 | 5/1988 | Graham et al. .......................... 435/7 |
| 4,788,138 | 11/1988 | Tung et al. ............................. 435/7 |
| 4,966,839 * | 10/1990 | Kaspar ................................... 435/7 |
| 5,089,423 * | 2/1992 | Diamandis et al. .................. 436/518 |
| 5,253,336 | 10/1993 | Yamada ................................ 395/142 |
| 5,382,530 | 1/1995 | Romelli et al. ...................... 436/500 |
| 5,420,042 * | 5/1995 | Schafer et al. ....................... 436/517 |
| 5,554,539 | 9/1996 | Chadney et al. ......................... 436/8 |
| 5,583,055 | 12/1996 | Oh et al. .............................. 436/517 |
| 5,585,241 * | 12/1996 | Lindmo ................................... 435/6 |
| 5,705,353 | 1/1998 | Oh et al. ............................. 435/7.92 |
| 5,723,346 * | 3/1998 | Frengen .............................. 436/523 |
| 5,739,042 * | 4/1998 | Frengen .............................. 436/523 |
| 5,948,368 * | 9/1999 | Hirai et al. ........................... 422/119 |

* cited by examiner

Primary Examiner—Christopher L. Chin
Assistant Examiner—Pensee T. Do
(74) Attorney, Agent, or Firm—Leland K Jordan (57) ABSTRACT

Calibrating an immunoassay by generating two reaction rate measuring curves, from samples having higher and lower relative levels of antigen, extrapolating a combination of the curves to cover sample concentrations known to contain an excess of antigen relative to an amount of capture reagent and combining the low end linear potion of the higher reaction rate measuring curve with the higher end portion of the extrapolated reaction rate measuring curve, thereby eliminating measuring inaccuracies otherwise arising from the hook effect. For antigen concentrations higher than the assay range, a high antigen signal utilizing the two rates avoids reporting false results.

14 Claims, 6 Drawing Sheets

METHOD FOR EXTENDING THE RANGE OF AN IMMUNOASSAY

CROSS-REFERENCES TO RELATED APPLICATIONS

This application is a continuation-in-part of Ser. No. 09/166,026, filed Oct. 5, 1998 now abandoned.

BACKGROUND OF THE INVENTION

1. Field of the Invention

The present invention relates to a method for obtaining immunoassay measurements for samples having an extended antigen concentration range and for providing a signal at high antigen levels. In particular, the present invention provides a calibration method to provide a linear correlation between two turbidimetric measurements made on samples having a high antigen concentration.

2. Description of the Related Art

Agglutination reactions have long been used in immunoassays to measure the concentration or presence of a wide variety of bacteria, cell-surface antigens, serum proteins or other analytes of clinical interest. Agglutination results from the reaction of bivalent antibodies with multivalent antigens of interest to produce aggregates which can be detected and measured in various ways. Similarly, the same reaction can be utilized for the detection of specific antibodies by the agglutination reaction caused by the addition of the corresponding antigen.

Increased sensitivity to visual or instrumental detection of agglutination or its inhibition can be achieved by the use of particle reagents as carriers, rather than soluble proteins or protein conjugates. Antibody particle reagents are also known. A common method for preparation of such reagents is by adsorption of the antibodies onto the surface of suitable adsorbents. Polystyrene-based latex particles have been used extensively for this purpose.

Immunological techniques for the detection of antigens by reaction with antibodies are known to be adversely affected by the well-known and so-called "hook effect" which introduces nonlinearity in agglutination reactions for sample having at high antigen concentrations. In these reactions, the particle-antibody reagent is provided in sufficient concentration to ensure that sufficient binding sites are available to capture all antigens within the sample. However, patient samples may contain a unusually high concentration of antigens so that all available antibodies within the particle reagent become attached to antigens. In this instance, further increasing antigen concentration results in a increase in immobilized label until the antigen concentration becomes so great that fewer sandwich complexes are formed resulting in an erroneous indication of the antigen concentration actually present in the sample. In these instances, the production of an linear assay calibration curve creates special problems because when the antigen is present in such an "excess" amount, it cannot act as the limiting factor in the reaction, thus producing a highly non-linear calibration curve.

Conventional immunoassay methods have attempted to address the hook-effect problem by supplying greater numbers of both the labeled and immobilized ligand binding partners in order to accommodate greater ligand concentrations. This approach, however, disadvantageously results in greater economic costs and is further constrained if the amount of ligand binding partners which may be immobilized per unit area on a solid phase is limited. Such increased concentrations may also be at the expense of sensitivity since increasing the numbers of binding partners and the area available for attachment of binding partners can result in inefficiencies in forming ligand-binding partner complexes with the few ligands that may be present in a sample having a very low ligand concentration.

Various attempts have been made to produce linear calibration curves in immunoassays which measure antigen concentrations that may not generate a linear reaction. One approach is to adjust the amount of insolubilized particle reagent thereby increasing the antibody concentration so that the antigen becomes the rate-limiting factor in the system; however, there is a limit to the amount of reagent that may be added without adversely affecting assay sensitivity. Another approach is the addition of excess labeled antibody, however, this increases the background level of the standard immunoassay. A third approach manipulates the calibration curve in order to achieve a relatively linear curve using a technique known as logit transformation to produce a semi-logarithmic plot of the relationship between absorbance and antigen quantity. In such a plot, the relationship between absorbance and antigen concentration can be approximated by a linear function, in a limited analytical range. While a linear approximation of the transformed curve can be made based on this approach and a conversion factor can be calculated from the data, the necessity of running a full standard curve, rather than a single standard, remains.

U.S. Pat. No. 4,595,661 discloses an improved immunoassay for a antigen in a fluid which comprises contacting the fluid with at least one first entity selected from a group consisting of an antibody (Ab) to the antigen (Ag), a soluble, labeled antibody to the antigen, and an antibody to the antigen bound to a solid carrier. The immunoassay is characterized in that the fluid is contacted with at least one additional entity selected from a group consisting of at least one different type of soluble, labeled antibody to the antigen, at least one different type of antibody to the Ag bound to a solid carrier, and at least one different type of antibody to the Ag. Each of the additional entities has an average affinity constant for the Ag lower than the K of its corresponding first entity for the Ag. In addition, the additional entity is present in an amount sufficient to avoid the hook effect.

U.S. Pat. No. 4,743,542 discloses a method for reducing the hook effect in immunoassays which is especially useful for immunoassay systems for the detection of ligands wherein the order of reactions, volumes of reactants, and number of wash steps are kept constant between ligand assays. The disclosed immunoassay reactants preferably include a haptenated ligand binding partner specific for the ligand to be detected and an insoluble, isotactic surface means for immobilizing said haptenated first binding partner. The reactants further include a reaction component having an enzyme label associated therewith and which becomes associated with said first binding partner in accordance with the presence or absence of the ligand to be detected. The method comprises adjustment of the reactants by addition to the aforedescribed reactants, ligand binding partner without associated hapten or, reaction component without associated enzyme label, or a combination thereof.

U.S. Pat. No. 4,788,138 is a method for improving measurement accuracy in which excess first antibody not bound to the solid support and/or excess unlabelled unbound second antibody are added to the immunoassay system. The first unbound unlabelled antibody acts as an analogue for the first antibody bound to the insoluble support. The first unbound unlabelled antibody may be a different antibody from the first antibody which is insolubilized. The unbound unlabelled second antibody may be a different antibody from the labeled second antibody for which it acts as an analogue. The addition of first antibody not bound to the insoluble support is not limited by the surface area available on the insoluble support. The addition of unlabelled unbound second antibody will not increase the background of the immunoassay. The addition of one or both of these analogues will, however, enable one to achieve a pseudo first-order reaction and, thus, a linear standard curve.

U.S. Pat. No. 5,358,852 discloses a specific binding immunoassay method in which a liquid sample containing C-reactive protein (CRP) in the presence of calcium ions is combined with a first antibody Ab1 specific for CRP and immobilized on a water-insoluble substrate and a labeled, unbound second antibody Ab2 specific for CRP to obtain a water-insoluble complex of Ab1, CRP, and Ab2. The water-insoluble complex is separated from the liquid sample and unreacted Ab2 followed by measuring either the amount of Ab2 associated with said water-insoluble complex or the amount of unreacted Ab2 as an indication of the amount of CRP in the sample. The presence of calcium ions improves the signal system of a sandwich assay specific to CRP sufficient to avoid the so-called "hook" effect. The CRP may be quantified whether present in the specimen at a very low or a very high concentration without risk of false negative results when CRP is present in high concentrations. Further, the presence of calcium has not been found to interfere with the measurement of CRP when CRP is present in low concentrations in the sample.

Accordingly, from a study of the different approaches taken in the prior art to the problems presented by the necessity for providing an actual linear standard curve in immunoassays designed to detect and/or measure antigen present in sufficient quantity such that prior art adjustments to the immunoassay system fail to yield a linear standard curve, there remains a need for an improved approach to provide liquid samples to an automated clinical analyzer without introducing complex control mechanisms and without unduly adding to the resources required.

SUMMARY OF THE INVENTION

Many of these disadvantages within the prior art are overcome by using the apparatus and methods of this invention. A calibration method has been discovered that consists of generating two reaction rate measuring curves, the first curve generated using a sample of higher volume and the second curve using the same sample having a smaller volume. A mathematical relationship is established between the two curves covering a low range of sample concentrations. From this relationship, a reaction rate measuring curve may be extrapolated to cover sample concentrations known to contain an excess of antigen relative to an amount of capture reagent. A final combined reaction rate measuring curve may be achieved by combining the low end linear potion of the first reaction rate measuring curve with the higher end portion of the extrapolated reaction rate measuring curve, thus eliminating measuring inaccuracies otherwise arising from the hook effect. In operation, a trip point or trip reaction rate is established at the junction of the low end potion of the first reaction rate measuring curve and the higher end portion of the extrapolated reaction rate measuring curve. If the reaction rate measured on a patient sample is below the trip point, the low end potion of the first reaction rate measuring curve is used to provide analytical results. Since higher volume is used in the first reaction, using the low potion of the first reaction decreases the limit of detection or increases sensitivity. On the other hand, if the reaction rate measured on a patient sample is higher than the trip point, the extrapolated reaction rate measuring curve is used to provide analytical results.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
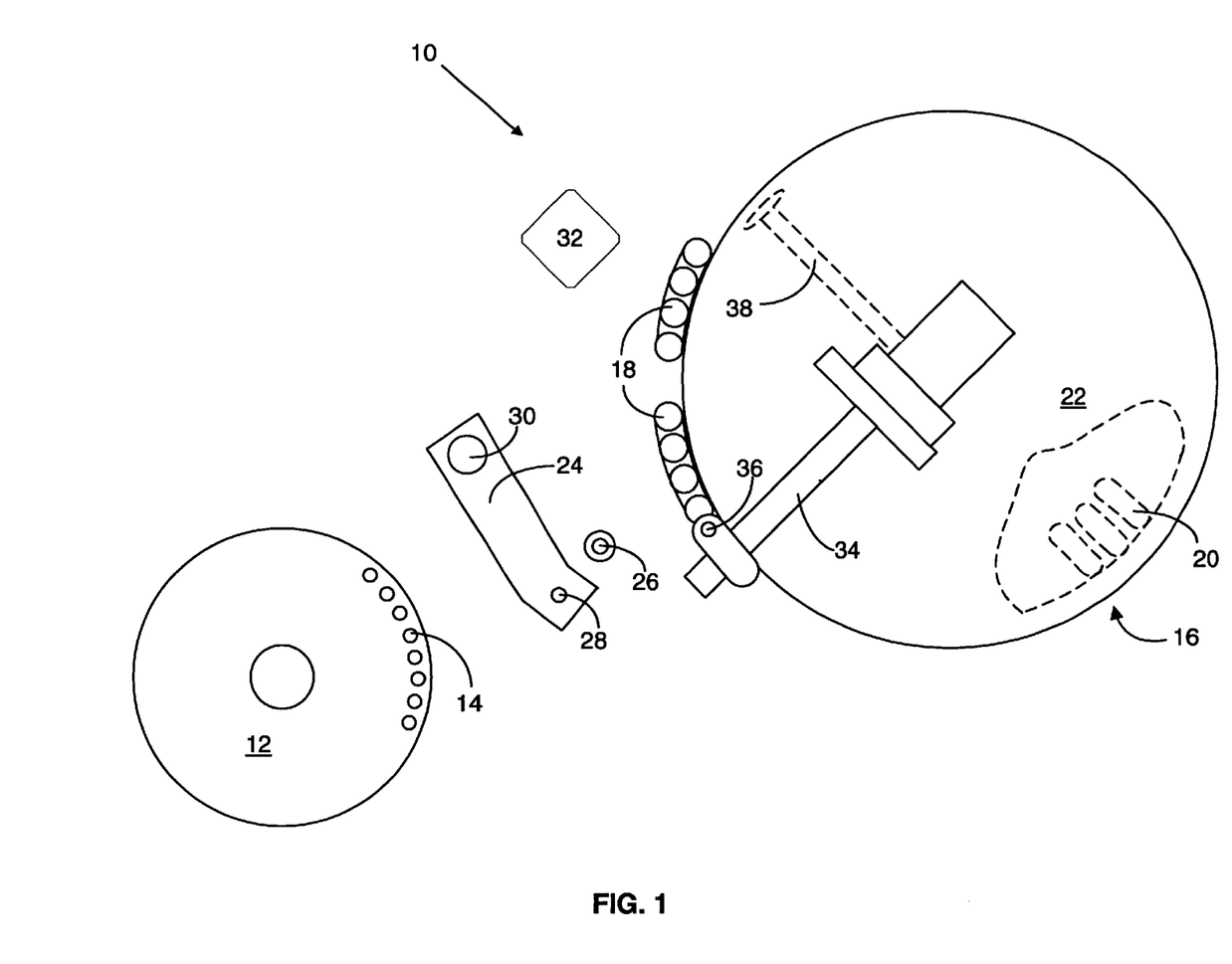
FIG. 1 is a schematic view of an automated immunoassay system in which the present invention may be used to advantage.

FIG. 1 shows schematically the elements of a convention automatic chemical analyzer 10 like that sold under the tradename Dimension® clinical chemistry system by Dade Behring Inc., Newark, Del., comprising a sample cup carousel 12 supporting a plurality of sample cups 14, a cuvette carousel 16 adapted to receive a plurality of cuvettes 18 and a plurality of reagent liquid cartridges 20 illustrated in dashed lines disposed beneath a lid 22 which covers various thermally controlled areas. Cuvettes 18 are formed by pulling two different composition ribbons of clear film from a cuvette film cartridge, not shown, onto the periphery of the cuvette carousel 16. The cuvette carousel 16, preferably in the form of a wheel, has about 100 separate cuvette cavities, the inner wall of each cavity having an opening to allow transmission of light. A small opening remains at the top of the cuvette 18 to allow the addition of reagent liquid and sample liquid. A sample liquid arm 24 and a wash resource 26 are located proximate the sample cup carousel 12 and cuvette carousel 16. Sample liquid arm 24 supports a conventional liquid probe 28 and is mounted to a rotatable shaft 30 so that movement of sample liquid arm 24 describes an arc intersecting the three components 14, 18, and 26. A separate analysis module 32, for instance an ion-selective electrode based device useful for measuring fluid ionic content of samples and comparing with standard fluids may be included within automatic chemical analyzer 10 and also be accessible by sample liquid arm 24.

A liquid probe 34 is rotatably mounted above cuvette carousel 16 and is adapted to draw reagent liquid from an appropriate reagent liquid cartridge 20 and deposit reagent liquid within a predetermined cuvette 18. Probe 34 further comprises an ultrasonic mechanism 36 used for hydrating, aspirating, dispensing and mixing reagents. The hydrating, aspirating, dispensing and mixing mechanisms have features well known in the art and need not be described further.

Photometric analyzing means 38 shown in dashed lines and located beneath the cuvette carousel 16 measures light absorbency through the cuvette 18 at various wavelengths, from which the presence of antigen in the sample liquid may be determined using well-known analytical techniques.

A preferred measuring means 38 of this invention is by turbidity employing a spectrophotometer to measure increased absorbance due to the increasing particle size resulting from the agglutination reaction. This increased absorbance is a direct measure of the agglutination caused by the antigen or an indirect measure of the agglutination inhibition caused by the antigen.

Figure 2:
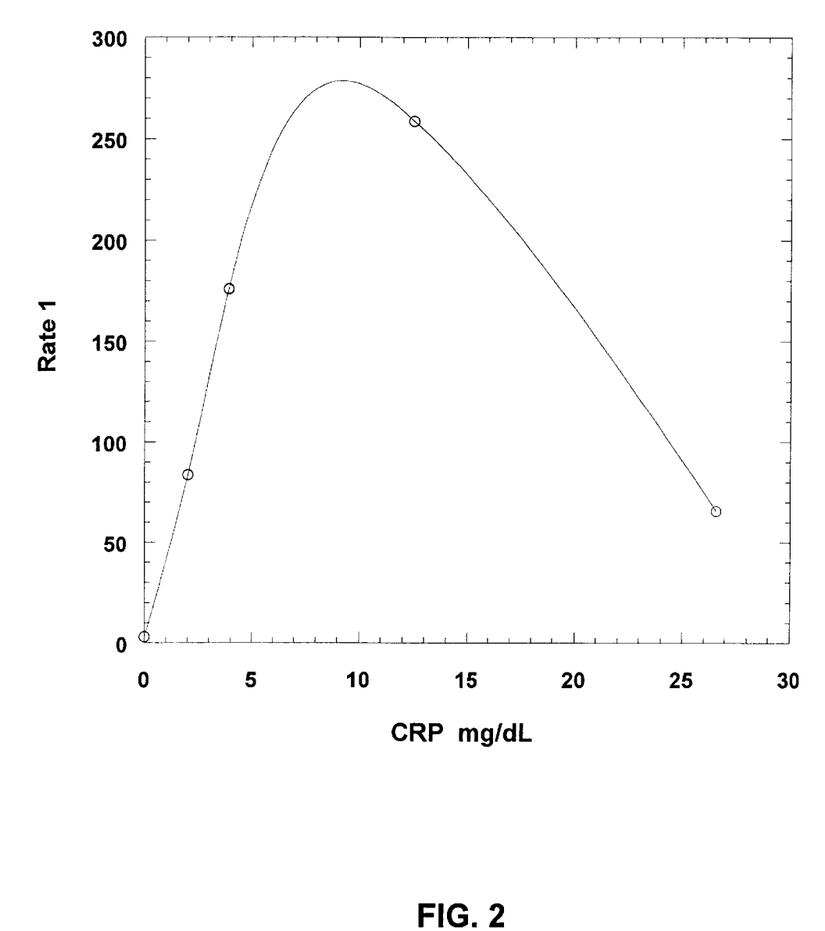
FIG. 2 is a reaction rate measuring curve generated using a sample of higher volume.

FIG. 2 shows the results of a reaction rate measuring experiment generated using a sample of larger volume as explained herein below.

Polyvinylnapthalene particles with covalently coupled polyclonal goat anti-human CRP antibodies are added to a potassium phosphate buffer containing 0.5% sulfhydryl free bovine serum albumin having pH=7.5 into the first reaction cuvette. About sixty seconds later, 8 uL of calibrator are added into the reaction cuvette to start the particle agglutination reaction. The turbidity is monitored at 340 nm and conventionally blanked or corrected using a measurement at 700 nm to correct for a variety of background measurement readings. Two photometric readings are taken approximately 30 and 230 seconds after the start of the reaction. The agglutination rate is calculated from the difference between the two readings divided by the time interval (about 200 seconds).

Figure 3:
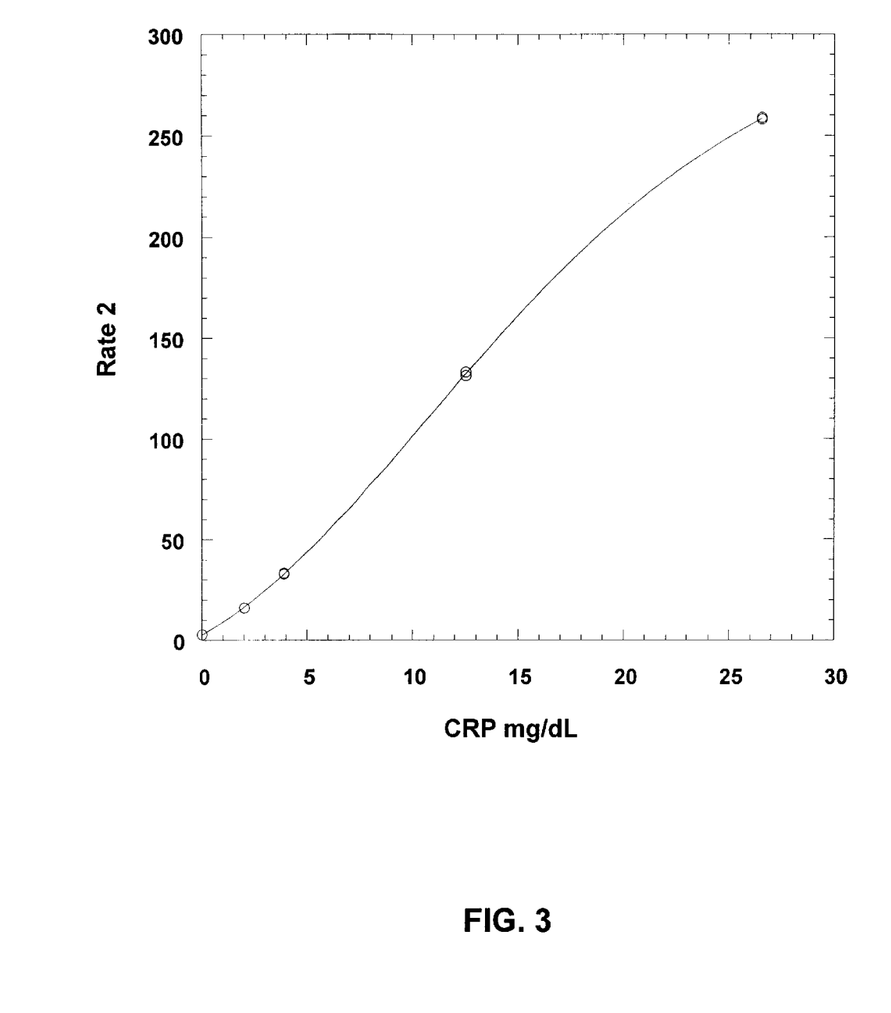
FIG. 3 is a reaction rate measuring curve generated using a sample of lower volume.

Five levels of calibrator containing 0.00, 2, 3.89, 12.53, and 26.57 mg/dL of C reaction protein (CRP) were used to generate the curve shown in FIG. 2. Rate 1 was generated using a sample of larger volume and showed a higher initial slope compared to that of Rate 2 generated using a sample of lower volume as seen in FIG. 3 Use of the larger volume sample thereby providing an improved sensitivity over using a sample of smaller volume. At 0.00 mg/dL, the sensitivity using 8 uL of sample volume (Rate 1) was improved from 0.17 mg/dL to 0.02 mg/dL as compared to using 2 uL of sample volume (Rate 2). These volumes are representative of the magnitude of difference intended by the terms "larger" and "smaller".

FIG. 3 illustrates a similar reaction rate measuring curve generated using the same sample as in FIG. 2 but having a smaller volume. Polyvinylnapthalene particles with covalently coupled polyclonal goat anti-human CRP antibodies were added with potassium phosphate buffer containing 0.5% sulfhydryl free bovine serum albumin, having pH=7.5 into a second reaction cuvette. About 60 seconds later, 2 uL of calibrator were added into the cuvette to start the particle agglutination reaction. The turbidity was monitored at 340 nm and blanked by 700 nm as described above. Two photometric reads were taken approximately 30 and 230 seconds after the start of the reaction. The agglutination rate was calculated from the differences between the two reads divided by the time interval (about 200 seconds).

Five levels of calibrator containing 0.00, 2.00, 3.89, 12.53, and 26.57 mg/dL of C reaction protein (CRP) were used to generate the curve. The purpose of reacting with a smaller sample volume is to eliminate or minimize the immunological "hook" within the expected assay range that occurs when reacting with the larger sample volume. FIG. 3 shows that the assay range, which otherwise would be below 12 mg/dL using 8 uL sample, can be extended to and beyond 26.57 mg/dL by using 2 uL sample.

Figure 4:
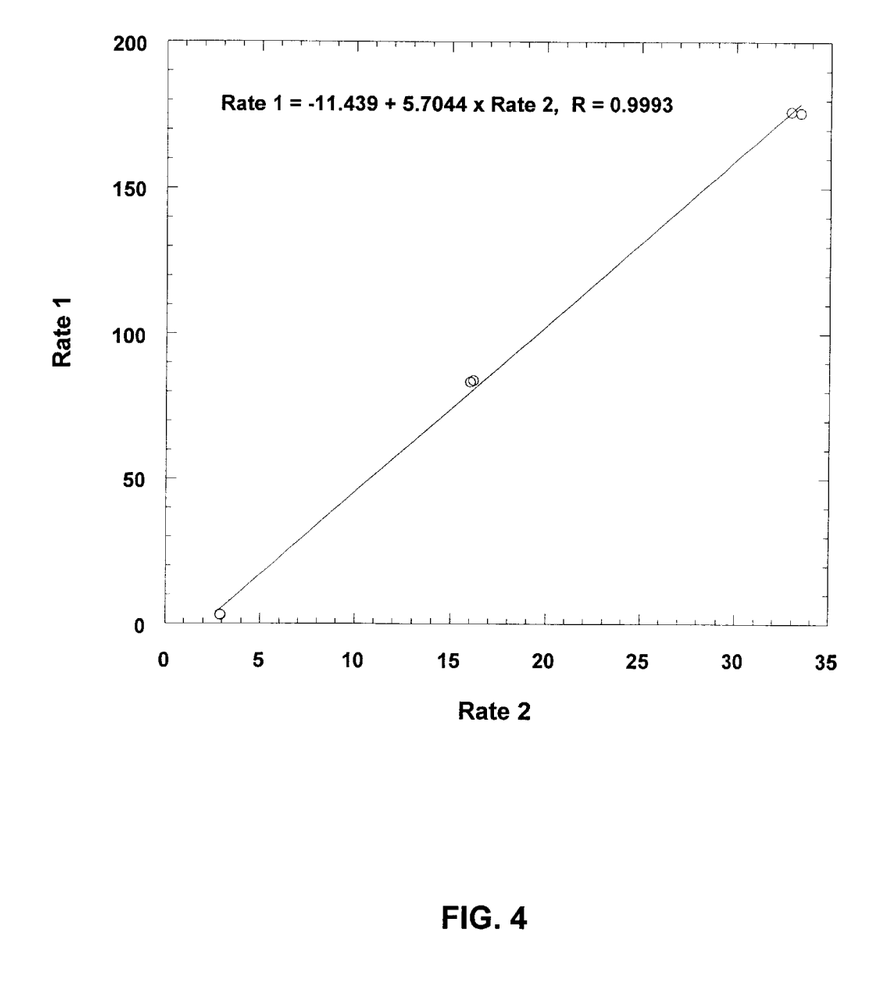
FIG. 4 is a linear regression between the rates of the first reaction and the second reaction for the lower levels of calibrator; and, FIG. 5 is a reaction rate measuring curve of the present invention achieved by combining the low end linear potion of the reaction rate measuring curve of FIG. 2 with the higher end portion of the extrapolated reaction rate measuring curve of FIG. 3 using the relationship established in FIG. 4.

FIG. 4 shows the results of a regression analysis between the rates of the first reaction and the second reaction for the lower 3 levels of calibrator. A mathematical relationship was established by conventional linear curve fitting techniques. The slope and intercept generated are used to extrapolate the combined reaction rate for samples having an antigen level or concentration that is higher than that in Level 3.

Figure 5:
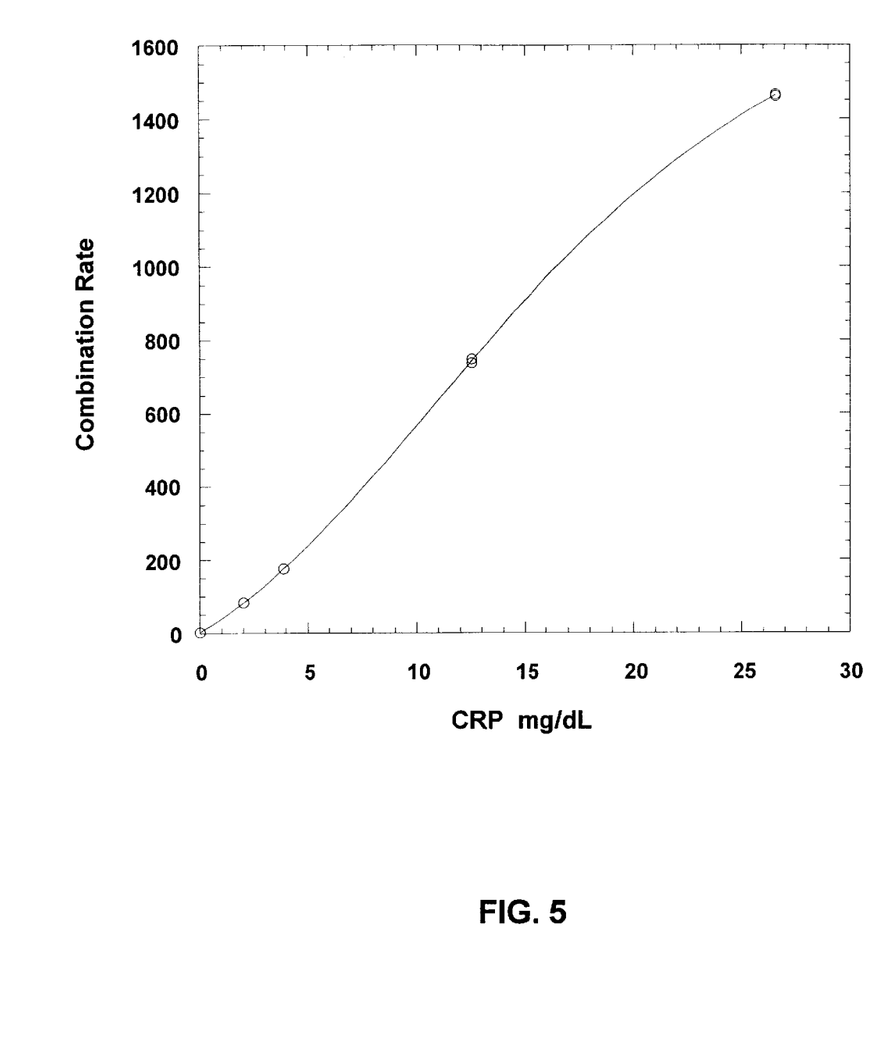

FIG. 5 is a reaction rate measuring curve exemplary of the present invention achieved by combining the low end linear potion of the reaction rate measuring curve of FIG. 2 with the higher end portion of the extrapolated reaction rate using the linear equation established in FIG. 4. and reaction rate measuring curve of FIG. 3.

The combined curve is produced as seen in Table 1.

TABLE 1

| CRP mg/dL | Rate 1 | Rate 2 | Combined Rate | Comment |
|---|---|---|---|---|
| 0.00 | 3.14 | 2.90 | 3.14 | Rate 1 is used |
| 2.00 | 83.75 | 16.08 | 83.75 | Rate 1 is used |
| 3.89 | 176.00 | 33.12 | 176.00 | Rate 2 is the trip point, Rate 1 is used |
| 12.53 | 258.65 | 132.39 | 743.74 | Extrapolated Rate 1 |
| 26.57 | 65.84 | 258.57 | 1463.53 | Extrapolated Rate 1 Rate 2/Rate 1 = 3.93 |

An extrapolated rate is calculated from Rate 2 using the following equation (1):
Extrapolated Rate 1 = slope × Rate 2 + intercept (1)

where slope and intercept are established by linear regression between Rate 1 and Rate 2 for the lower levels (either the lower 2, 3, or 4 levels). In this example, the linear regression was established between the lower three levels. The slope and intercept obtained based on the data in Table 1 are 5.705 and −11.454, respectively.

To generate a combined standard curve, a trip point or trip rate is established such that if Rate 2 is equal to or lower than the trip point, Rate 1 may be safely used "as is", without further adjusting. However, if Rate 2 is greater than the trip point, an extrapolated Rate 1 is generate by equation (1). Rate 1 may then be used along with extrapolated Rate 1 are used to establish a standard curve.

In the above example, Rate 2 at 3.89 mg/dL CRP was used as the trip point. In general, the Rate 2 for the highest level used in the linear regression is the trip point. Rate 2, instead of Rate 1, is preferably selected for the trip point because Rate 2, by the nature of its smaller volume does not "hook" within assay range where Rate 1 does. Thus, reporting falsely low results in the presence of high antigen is avoided within the assay range by using a Rate 2 as the trip point.

By design, Rate 1 is generated by larger sample volume (8 uL) that improves sensitivity at low antigen but causes hook effect (at about 10–12 mg/dL) within the expected assay range (26.57 mg/dL). Rate 2 is generated by smaller volume (2 uL) that extends the "hook" beyond the assay range (to about 40 mg/dL) but with a loss of sensitivity at low antigen. The advantage of the combined curve is that it utilizes the low antigen portion of Rate 1 to improved sensitivity and high antigen portion of Rate 2 to extend the assay range beyond the hook region for Rate 1 (as reflected by the extrapolated Rate 1). Thus, an assay with extended assay range and improved sensitivity at low antigen is formed.

Figure 6:
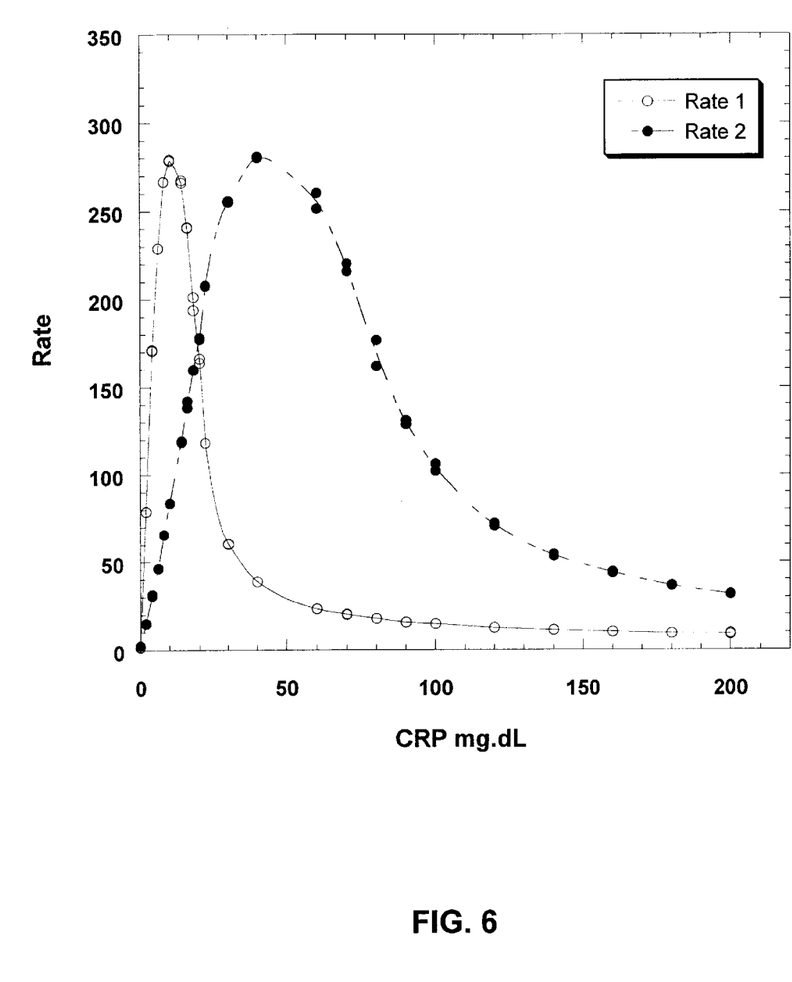
FIG. 6 is reaction rate measuring curve illustrating the use of a high antigen signal.

FIG. 6 illustrates the use of a high antigen signal that alerts instrument operators for false low results generated by a sample containing antigen above the assay range due to hook effect. The signal compares the rates of the two reactions in the 1st and 2nd cuvette, generating an error message for antigen concentrations from just above the assay range to 200 mg/dL CRP and beyond. Within the art, it is generally accepted that no patient has been found to have CRP levels higher than 200 mg/dL.

The high antigen signal consists of two steps:

1) The ratio of Rate 2/Rate 1 of a sample is calculated by the instrument and compared to that of the highest calibrator level (3.93 in Table 1). If the ratio of the sample is greater than that of the calibrator level plus an empirically determined factor, high antigen signal is tripped. The empirically determined factor is established to be 0.5 to cover random variations in the ratio of the highest calibrator level. In the example shown in Table 1, 4.43 is the number that the ratio of a sample is compared to. This condition can signal antigen concentrations around the peak of hook region. In the CRP example, it can go from the upper assay range to 140 mg/dL CRP.

2) Since the first step does not signal up to 200 mg/dL which is the safe concentration to cover all kinds of patients, a second step is designed to signal higher antigen concentration. Because Rate 2 is always higher than Rate 1 in the presence of high antigen by about 10 rate and at very high antigen, Rate 2 is always less than 120 rate in this assay, the following statement is used in this step:

If Rate 2 is <120 and (Rate 2–Rate 1) >10, conventional electronics may be used to signal or display a high antigen condition.

In FIG. 6, the overlap region of step 1 and 2 signals ensures that all of the samples containing high antigen will be signaled. This high antigen signal signals all the samples containing antigen level between above the assay range to 200 mg/dL or higher.

As illustrated in FIGS. 2–6, the present invention may be practiced as follows.

A calibration of the analytical instrument used is made before measuring a patient sample. Calibration typically includes at least three solutions having known concentrations of antigen in order to obtain a combined calibration curve. The combined rates obtained (e.g. as described in FIG. 5) and the known concentrations of antigen are used to generate coefficients using a mathematical model (logit, linear, etc.). A sample of serum or plasma specimen is drawn from a patient who is suspected to have either a normal or abnormal antigen concentration.

To measure the antigen concentration, a first patient sample of larger volume (8 uL in the example) and a second patient sample of smaller volume (2 uL in the example) are respectively added into two separate cuvettes that contain antibody attached particles and reaction buffer. The turbidity increase due to the particle agglutination in the presence of antigen is measured at the wavelength of 340 nm and blanked at the wavelength of 700 nm. Rate 1 and Rate 2 are generated from reaction 1 and reaction 2, respectively. Rate 2 is compared to the trip point from the calibration (e.g. in FIG. 5, the trip point is 33.12), and if Rate 2 is less than the trip point (e.g. 20.00), Rate 1 is used to calculate antigen concentration in the sample with the appropriate calibration coefficients. If Rate 2 is greater than the trip point (e.g. 90.00), equation (1) is used to calculate an extrapolated Rate 1, and this extrapolated Rate 1 is used within the instrument to calculate antigen concentration with the calibration coefficients. If the antigen concentration is above the assay range, the high antigen signal is automatically tripped or otherwise displayed to avoid reporting false low result due to hook effect.

The following examples are given to help a complete understanding of this invention and are provided herein for purposes of illustration only and are not intended to be limiting in any manner.

EXAMPLES

(1) Preparation of an Anti-CRP-sensitized Latex Reagent

To 10 ml of a solution of anti-CRP antibody in a phosphate buffer (concentration 15 mM, pH 7.5), 0.33 ml of polystyrene latex particle solution having an average diameter of 48 nm was added, and the mixture was stirred for 3 hours at 37° C. The mixture was purified by centrifugation at 28,000 r.p.m for 2 hours and re-suspends in a particle diluent which contains 0.0089% SDS and 200 mM glycine, pH 7.5. Final solution contains 0.45% solid particles with 2 mg/mL antibody loading.

(2) Preparation of a Calibration Curve

Each calibrator level used two cuvettes. In the first cuvette, an 80 uL aliquot of the anti-CRP-latex particle reagent prepared in part (1) above was mixed with a 168 uL aliquot of 245 mM potassium phosphate buffer containing 0.5% sulfhydryl free bovine albumin of pH=7.5. A 2 uL of the calibrator solution was added and two turbidimetric measurements were taken at 340 nm and were blanked at 700 nm. The reaction rate was calculated by the turbidity difference between the two measurements. The rate generated from the first cuvette is Rate 1. In the second cuvette, an 80 uL aliquot of the anti-CRP-latex particle reagent prepared in part (1) above was mixed with a 168 uL aliquot of 245 mM potassium phosphate buffer containing 0.5% sulfhydryl free bovine albumin having pH=7.5. An 8 uL sample of the calibrator solution was added and turbidimetric measurements were taken at 340 nm and blanked at 700 nm The reaction rate was calculated by the turbidity difference between the two measurements. The rate generated from the second cuvette is Rate 2. In this experiment, five levels of calibrator solution was used as shown in the following Table 2.

TABLE 2

| CRP mg/dL | Rate 1 | Rate 2 | Combined Rate | Comment |
|---|---|---|---|---|
| 0.00 | 2.77 | 2.72 | 2.77 | Rate 1 is used |
| 2.00 | 83.52 | 15.55 | 83.52 | Rate 1 is used |
| 3.89 | 175.25 | 32.58 | 175.25 | Rate 2 is the trip point Rate 1 is used |
| 12.53 | 257.33 | 130.27 | 739.24 | Extrapolated Rate 1 |
| 26.57 | 62.51 | 256.81 | 1467.43 | Extrapolated Rate R1 Rate 2/Rate 1 = 4.11 |

Linear regression between Rate 1 and Rate 2 was done by using levels 0.00, 2.00, and 3.98 mg/dL solutions and the least square curve fitting.

$$\text{Extrapolated Rate 1} = 5.754 \times \text{Rate 2} - 10.354 \quad (2)$$

where slope and intercept are established by regression analysis between Rate 1 and Rate 2 for the lower 3 levels. The trip point is 32.58, which is the Rate 2 at the third level. To generate a combined standard curve, the Rate 2 for a sample is compared to the trip point. If the Rate 2 is equal or lower than the trip point, the Rate 1 is used "as is", as in the case for the first three calibrator solutions (Table 2). For a Rate 2 that is greater than the trip point, an extrapolated Rate 1 is generate by equation (2), as in the case of level 4 and 5. The combined rate and the standard antigen concentrations for the calibrator solutions were used for logit curve fitting where the following equation was used:

$$[\text{Antigen}](\text{mg/dL}) = C3 \times \{[C1/(CR-C0)-1]^{1/C2} - 0.5\} \quad (4)$$

Where
C0=−149.46;
C1=2101.2;
C2=−3.6747;
C3=29.911

(3) Assay of CRP in Samples

Serum samples were used in this example and assayed using the above described the two reaction approach. No sample is diluted in this study. Samples Number 7 to 12 were normal human serum pool spiked with purified CRP obtained from Scipac Co. and based on their bottle values, an additional 40, 60, 100, 140, 180, and 200 mg/dL CRP were spiked respectively into the normal human serum pool to generate samples number 7 to 12. Sample number 1 to 6 are human serum samples containing varying amount of CRP. To measure the sample, the trip point, 32.58, from the calibration is used.

Every Rate 2 measured for each sample is compared to the trip point, and if it is less than or equal to 32.58, Rate 1 for that sample is used to calculate the CRP concentration with the appropriate calibration coefficients. If Rate 2 is greater than 32.58, equation (2) is used to calculate an extrapolated Rate 1. Sample 6 was measured to contain 26.34 mg/dL CRP which is still within the assay range so the high antigen signal was not tripped or displayed. Samples 8 to 12 contained CRP higher than 26.57 mg/dL which is the highest calibrator concentration, so all of these sample tripped the high antigen signal (Table 2). The antigen signals used were:

Step 1: if Rate 2/Rate 1>4.61, high antigen is indicated; and,

Step 2: if Rate 2 is less than 120, and (Rate 2−Rate 1) is greater than 10, high antigen is indicated.

The number 4.61 is generated by analyzer 10 during calibration and is the ratio of Rate 2/Rate 1 (=4.11) plus 0.5 (the empirically determined factor to cover the ratio variation) for the highest level calibrator. Step 1 flagged samples 7 to 10. Step 2 flagged samples 9 to 12. Both steps flagged samples 9 and 10. Step 1 and 2 signal high antigen independently, therefore, as long as one condition is satisfied, high antigen is signaled, as illustrated in Table 3.

4) In an alternative embodiment, a more continuous or graduated switch from using straight R1 to the extrapolated R1 may be employed for calculating the combined rate for samples with CRP values near or around the trip point to minimize imprecision that may be caused by the single step switch during calibration procedures as described hereinbefore. An example of using a single step switch during calibration as a graduated switch is in Table 4, in which an empirically selected number of 1.2 has been chosen for a CRP assay, a value that was found to increase the sample analyses accuracy from about 6% C.V. to about 2% C.V. The empirically selected number depends on the linearity of regression between R1 and R2 at lower analyte concentrations, within different analysis methodologies.

TABLE 4

| Calibration (Single step switch) | Sample Analysis (Graduated switch) |
|---|---|
| If AR < trip, then combo mA = SR. | If AR < trip, then combo mA = SR. |
| If AR ≧ trip, then combo mA = extrapola SR. | If AR ≧ trip, and AR < trip + 1.2, then combo mA = [1 − (AR − trip)/ 1.2 × SR + [(AR − trip)/1.2] × extrapolated SR. If AR ≧ trip + 1.2, then combo mA = extrapolated SR. |

It is to be understood that the embodiments of the invention disclosed herein are illustrative of the principles of the invention and that other modifications may be employed which are still within the scope of the invention. For example, in one alternate exemplary embodiment, Accordingly, the present invention is not limited to those embodiments precisely shown and described in the specification but only by the following claims.

What is claimed is:

1. A method for generating a calibration curve for an immunoassay comprising:

separating a sample having an antigen concentration therein into a first larger volume portion and into a second smaller volume portion;

generating first and second reaction rate curves each curve having a low end antigen concentration portion and a high end antigen concentration portion, the first reaction rate curve generated from the first larger volume portion and the second reaction rate curve generated from the second smaller volume portion;

TABLE 3

| Sample | Rate 1 | Rate 2 | Rate 1/Rate 1 | Rate 2 − Rate 1 | Combined Rate | Analyte mg/dL | Antigen Flag |
|---|---|---|---|---|---|---|---|
| 1 | 83.52 | 15.55 | 0.19 | −67.97 | 83.52 | 2.02 | No |
| 2 | 171.13 | 31.19 | 0.18 | −139.94 | 169.34 | 3.77 | No |
| 3 | 266.82 | 65.98 | 0.25 | −200.84 | 369.31 | 7.13 | No |
| 4 | 240.88 | 140.19 | 0.58 | −100.69 | 796.36 | 13.37 | No |
| 5 | 165.13 | 177.82 | 1.08 | 12.69 | 1012.90 | 16.75 | No |
| 6 | 60.54 | 255.50 | 4.22 | 194.96 | 1459.89 | 26.34 | No |
| 7 | 38.94 | 280.60 | 7.21 | 241.66 | 1604.30 | N/R | Yes |
| 8 | 23.46 | 256.03 | 10.92 | 232.57 | 1462.92 | N/R | Yes |
| 9 | 14.79 | 104.19 | 7.05 | 89.40 | 589.20 | N/R | Yes |
| 10 | 11.35 | 54.01 | 4.76 | 42.66 | 300.45 | N/R | Yes |
| 11 | 9.43 | 36.59 | 3.88 | 27.16 | 200.21 | N/R | Yes |
| 12 | 9.18 | 31.69 | 3.46 | 22.51 | 9.18 | N/R | Yes |

(N/R indicates no reportable result.)

mathematically curve fitting the first and second curves in a low range of antigen concentrations for which both curves are linear;

extrapolating the first reaction rate curve for those antigen concentrations containing an excess of antigen relative to an amount of capture reagent used in the immunoassay to produce an extrapolated reaction rate curve having a low end portion;

combining the low end potion of the first reaction rate measuring curve with the higher end portion of the extrapolated reaction rate curve to produce a single curve; and, using the single curve as the calibration curve for an immunoassay thereby eliminating measuring inaccuracies otherwise arising from the hook effect.

2. The method of claim 1 further comprising:

establishing a trip point at the junction of the high end linear potion of the first reaction rate measuring curve and the low end potion of the extrapolated reaction rate measuring curve; and, using the low end linear portion of the first reaction rate measuring curve to provide analytical results if the reaction rate measured on a patient sample is equal to or less than the trip point and using the extrapolated reaction rate measuring curve to provide analytical results if the reaction rate measured on a patient sample is greater than the trip point.

3. The method of claim 1 wherein the antigen is C reactive protein.

4. The method of claim 2 wherein the antigen is C reactive protein.

5. The method of claim 3 wherein mathematically curve fitting the two curves in a low range of sample concentrations covers the antigen concentration range below about 100 mg/dL.

6. The method of claim 2 further including means for generating an excess signal in the instance that the antigen concentration within the sample exceeds the trip point.

7. The method of claim 4 wherein the trip point is in the range between 30 mg/dL and 35 mg/dL.

8. The method of claim 1 wherein mathematically curve fitting the two curves comprises use of a regression analysis.

9. The method of claim 1 wherein the immunoassay comprises a turbidimetric measurement.

10. The method of claim 1 wherein the immunoassay is an immunoassay for C reaction protein.

11. The method of claim 1 wherein high antigen concentration is signaled by using the ratio of two or more than two reaction rates.

12. The method of claim 1 wherein high antigen concentration is signaled by using the combination of the differences between the two reaction rates and the rate of one of the two reactions.

13. The method of claim 1 wherein high antigen concentration, not limited to antigen excess and with the cutoff limit determined as needed, is signaled.

14. The method of claim 4 wherein a graduated switch is employed for calculating the combined rate for samples with C reaction protein values near or around the trip point established during calibration.

* * * * *